(12) United States Patent
Li et al.

(10) Patent No.: US 7,672,813 B2
(45) Date of Patent: Mar. 2, 2010

(54) MIXED STATISTICAL AND NUMERICAL MODEL FOR SENSOR ARRAY DETECTION AND CLASSIFICATION

(75) Inventors: Sichu Li, Burlington, MA (US); Mary E. Tabacco, Brighton, MA (US)

(73) Assignee: Smiths Detection Inc., Boston, MA (US)

( * ) Notice: Subject to any disclaimer, the term of this patent is extended or adjusted under 35 U.S.C. 154(b) by 69 days.

(21) Appl. No.: 11/987,658

(22) Filed: Dec. 3, 2007

(65) Prior Publication Data

US 2009/0144022 A1   Jun. 4, 2009

(51) Int. Cl.
*H03F 1/26* (2006.01)
(52) U.S. Cl. ...................................... 702/189
(58) Field of Classification Search ................. 702/189, 702/191; 367/131; 382/106
See application file for complete search history.

(56) References Cited

U.S. PATENT DOCUMENTS

| | | | |
|---|---|---|---|
| 5,446,681 A | | 8/1995 | Gethner |
| 5,502,688 A | * | 3/1996 | Recchione et al. .......... 367/131 |
| 5,652,715 A | * | 7/1997 | Hanson ..................... 702/191 |
| 5,832,411 A | | 11/1998 | Schatzmann |
| 5,866,430 A | | 2/1999 | Grow |
| 6,480,795 B1 | | 11/2002 | Roman |
| 6,649,416 B1 | | 11/2003 | Kauer |
| 6,711,280 B2 | * | 3/2004 | Stafsudd et al. ............. 382/106 |
| 6,847,490 B1 | | 1/2005 | Nordstrom |
| 6,952,499 B1 | | 10/2005 | Vititoe |
| 6,952,657 B2 | | 10/2005 | Jahns |
| 6,961,677 B1 | | 11/2005 | Boysworth |
| 6,996,472 B2 | | 2/2006 | Wilkes |
| 7,006,923 B1 | | 2/2006 | Rubin |
| 7,046,359 B2 | | 5/2006 | Voigt |
| 7,076,383 B2 | | 7/2006 | Schafer |
| 7,120,226 B2 | | 10/2006 | Ledoux |
| 7,171,312 B2 | | 1/2007 | Steinthal |
| 7,224,825 B2 | | 5/2007 | Paradis |
| 7,244,902 B2 | | 7/2007 | Popp |
| 7,262,407 B2 | | 8/2007 | Miller |

(Continued)

FOREIGN PATENT DOCUMENTS

WO   WO 01/73616 A2   10/2001

(Continued)

OTHER PUBLICATIONS

International Search Report and Written Opinion mailed Jun. 5, 2009, received in corresponding International application No. PCT/US2008/085130.

*Primary Examiner*—Tung S Lau
*Assistant Examiner*—Xiuquin Sun
(74) *Attorney, Agent, or Firm*—Foley & Lardner LLP

(57) ABSTRACT

A method and system for detecting and classifying biosensor and chemical sensor data includes processing data fetched from an array of sensors. A statistical analysis of the processed data is performed, to obtain statistically analyzed sensor data. A determination is made, based on the statistically analyzed sensor data, whether or not there a response signal has been generated from the array of sensors. If a response signal is determined to have been generated, a numerical pattern recognition is performed on the data collected from the array of sensors, in order to categorize the data.

19 Claims, 2 Drawing Sheets

U.S. PATENT DOCUMENTS

| | | |
|---|---|---|
| 7,262,440 B2 | 8/2007 | Maier |
| 2003/0114986 A1 | 6/2003 | Padmanabhan et al. |
| 2004/0111220 A1 | 6/2004 | Ochs |
| 2004/0254736 A1 | 12/2004 | Michelson |
| 2005/0074834 A1 | 4/2005 | Chaplen |
| 2005/0151976 A1 | 7/2005 | Toma |
| 2005/0251347 A1 | 11/2005 | Perona |
| 2006/0229822 A1 | 10/2006 | Theobald et al. |
| 2006/0249683 A1 | 11/2006 | Goldberg |
| 2006/0256338 A1 | 11/2006 | Gratton |
| 2007/0005256 A1 | 1/2007 | Lincoln et al. |
| 2007/0055456 A1 | 3/2007 | Raftery |
| 2007/0081156 A1 | 4/2007 | Treado |
| 2007/0153268 A1 | 7/2007 | Panza |
| 2007/0241261 A1 | 10/2007 | Wendt |

FOREIGN PATENT DOCUMENTS

| | | |
|---|---|---|
| WO | WO 03/048725 A2 | 6/2003 |
| WO | WO 03/071942 A1 | 9/2003 |
| WO | WO 2004/030512 A2 | 4/2004 |

* cited by examiner

MIXED STATISTICAL AND NUMERICAL MODEL FOR SENSOR ARRAY DETECTION AND CLASSIFICATION

FIELD OF THE INVENTION

This invention is related in general to the field of biosensor and chemical sensor array detection and classification.

BACKGROUND OF THE INVENTION

Biosensor array units having sensor arrays are becoming very useful in today's society, with the threat of bioterrorism being more and more prominent. In more detail, bioterrorism and biological warfare pose both physical and psychological threats to military and civilian forces, as well as to civilian populations. Biological and chemical sensors also hold promise for environmental monitoring, indoor air quality assessment, and in food and beverage analysis.

Typically, either analytical or statistical models are utilized to generate a detection algorithm for sensor arrays. Analytical models are only applicable for quantitative data analysis while statistical models typically capture all correlations in the datasets of which some may be generated by causes that are not of interest. The sensitivity and specificity are highly dependent on operational conditions, and thus it is difficult to optimize the trade-off relationship between the detection sensitivity and specificity. In practice, it is often required to collect standard datasets to calibrate these models, and thus they are not ideal for operation under robust environments.

SUMMARY OF THE INVENTION

The present invention relates to a method and apparatus for sensor array detection and classification.

In accordance with one aspect of the invention, there is provided a method for detecting and classifying sensor data. The method includes performing a statistical analysis of the data collected from an array of sensors, to obtain statistically analyzed sensor data. Based on the statistically analyzed sensor data, it is determined whether or not there a response signal has been generated from the array of sensors. If a response signal is determined to have been generated, the method further includes performing a numerical pattern recognition on the data collected from the array of sensors, in order to categorize the data.

In accordance with another aspect of the invention, there is provided a system for detecting and classifying sensor data. The system includes a data processing unit configured to receive and perform data processing on data output from an array of sensors. The system also includes a statistical analysis unit configured to perform statistical analysis on the data processed by the data processing unit, to obtain statistically analyzed sensor data, wherein the statistical analysis unit determines, based on the statistically analyzed sensor data, whether or not there a response signal has been generated from the array of sensors. The system further includes a numerical pattern recognition unit configured to perform a numerical pattern recognition on the data collected from the array of sensors, in order to categorize the data.

In accordance with yet another aspect of the invention, there is provided a computer readable medium embodying computer program product for detecting and classifying sensor data, the computer program product, when executed by a computer, causing the computer to perform the steps of, fetching data collected from an array of sensors;

performing a statistical analysis of the data collected from the array of sensors, to obtain statistically analyzed sensor data;

determining, based on the statistically analyzed sensor data, whether or not there a response signal has been generated from the array of sensors; and performing, if a response signal is determined to have been generated, a numerical pattern recognition on the data collected from the array of sensors, in order to categorize the data.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention.

DETAILED DESCRIPTION

Reference will now be made in detail to embodiments of the invention, examples of which are illustrated in the accompanying drawings. An effort has been made to use the same reference numbers throughout the drawings to refer to the same or like parts.

Unless explicitly stated otherwise, "and" can mean "or," and "or" can mean "and." For example, if a feature is described as having A, B, or C, the feature can have A, B, and C, or any combination of A, B. and C. Similarly, if a feature is described as having A, B, and C, the feature can have only one or two of A, B, or C.

Unless explicitly stated otherwise, "a" and "an" can mean "one or more than one." For example, if a device is described as having a feature X, the device may have one or more of feature X.

Figure 1:
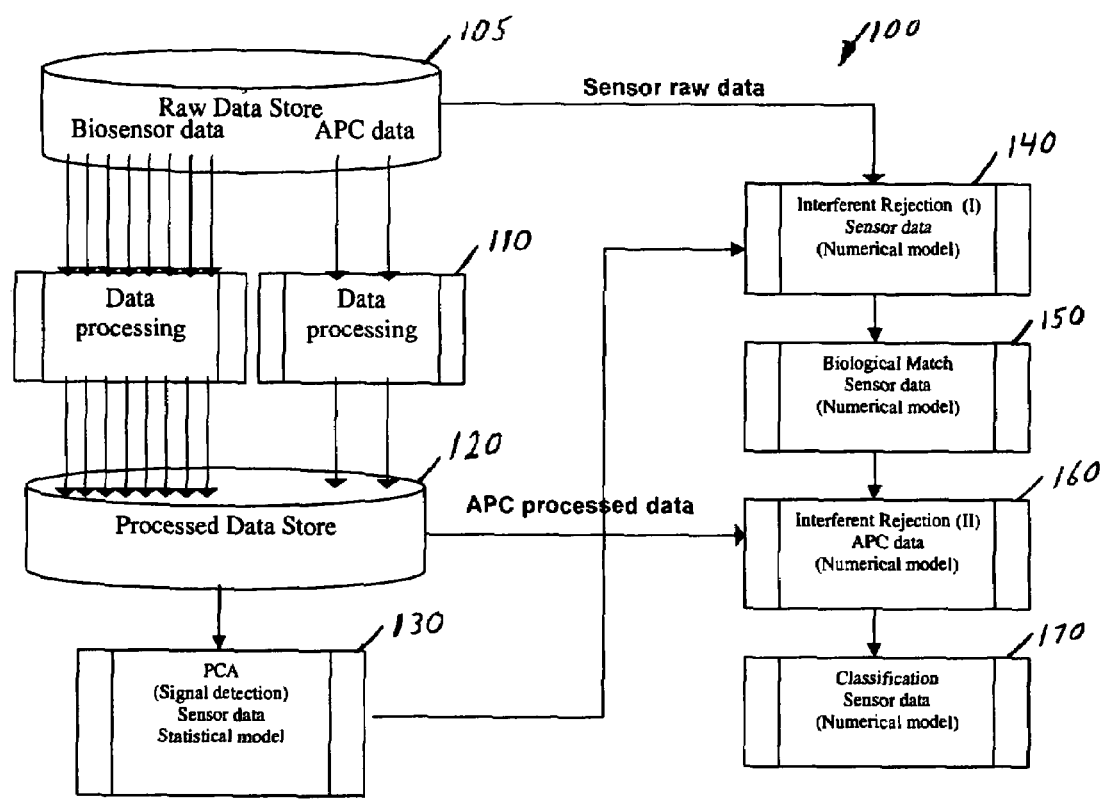
FIG. 1 is a block diagram showing elements involved in performing a statistical and numerical analysis of biosensor data, according to a first embodiment of the invention.

FIG. 1 shows a data analysis system that combines both statistical and numerical models have been developed as a detection and classification algorithm for a biosensor array, according to a first embodiment of the invention. The biosensor array used to provide data to the system according to the first embodiment may be a Smart Bio Sensor (SBS), and it may be a biosensor array of a handheld or portable sensor detection unit (e.g., Bioseeq or BioseeqPlus) made by Smiths Detection Inc., for example. The statistical analysis is utilized for sensor signal detection, while one or more numerical methods are applied to analyze the correlations of interest captured in the data for pattern recognition. The statistical analysis provides the detection sensitivity, and the numerical analysis enhances the biological recognition capability and thus provides the detection and classification specificity. The system, which may be implemented in Matlab and C programming language in one possible implementation of the first embodiment, can be run in real-time simultaneously with data collection. By way of example and not be way of limitation, in the first embodiment, 3 to 5 data points are utilized for detection analysis and 10 data points are utilized for classification analysis. The system according to the first embodiment is capable of carrying out self-calibration in real-time, and is thus suitable for robust operation. Other chemical/biological sensor arrays besides an SBS array may be utilized to provide sensor data to be detected and classified by way of the first embodiment.

As shown in FIG. 1, the system receives data collected from an array of sensor channels and stored in a data store, into a Principle Component Analysis (PCA) statistical model, to determine if there is a response signal. For a detected sensor response, the system runs a numerical pattern recognition model that may be customized based on the sensor responses that are of interest. Information from other sensor channels, such as airborne particle counter (APC) data, may also be stored (in the data store), interpreted and utilized as parameters in a pattern recognition model for interferent rejection. Fingerprints numerically extracted from the correlations between different biosensor channels can also be exploited for classification.

With the system according to the first embodiment, there is provided a detection and classification system for a biosensor array that is suitable for real-time and robust operation. Accordingly, no frequent model calibration needs to be done by users of a biosensor detection unit that incorporates the system and method according to the first embodiment.

In one possible implementation of the first embodiment, a statistical model Principal Component Analysis (PCA) unit is utilized for signal detection, and then a numerical model which is built upon correlations of interest captured in a biosensor dataset is run for pattern recognition to enhance the specificity of the detected sensor array data. The trade-off relationship between detection sensitivity and specificity can be optimized using a Relative Operating Characteristic (ROC) curve, for example.

Turning now to FIG. 1, in a system 100 according to the first embodiment, raw biosensor data obtained by an array of biosensors (not shown) is stored in a raw data store 105. The stored raw biosensor data is processed by a data processing unit 110, and the processed data is stored in a processed data store 120. A PCA unit 130 performs signal detection of the data-processed biosensor data, based on a statistical model. If a signal detection is determined to have occurred based on analysis by the PCA unit 130, a numerical analysis of the biosensor and APC data is then performed. In more detail, an interferent rejection I unit 140, a biological match sensor data unit 150, and an interferent rejection II unit 160 are used to perform numerical analysis on the statistically analyzed biosensor and the non-statistically-analyzed APC data, and a classification sensor data unit 170 is used to classify the numerically analyzed data (if determined to be required). The units 140, 150, 160 and 170 utilize different numerical models and collectively correspond to a numerical analysis unit of the system according to the first embodiment.

Also, as shown in FIG. 1, Airborne particle counter (APC) data is collected by an APC sensor (not shown), and stored in the raw data store 105. The stored raw APC data is processed by the data processing unit 110, and the processed data is stored in the processed data store 120, whereby the APC data is also statically analyzed and numerically analyzed by the system and method according to the first embodiment. The APC data is utilized for interferent rejection as determined by the interferent rejection II unit 160.

The biosensor data obtained by an array of biosensors provides fluorescence information, while the APC data provides a total count of particles per liter of air. Thus, the biosensor data and the APC data are measures of different physical properties. Given the entirely independent nature of the data, different approaches are required to process these data. In one possible implementation of the first embodiment, the biosensor data processing is processed by a Savitzky_Golay filter to smooth the data and remove the offset, whereby this filtering corresponds to the data processing performed on raw biosensor data by the data processing unit 110. Also, in one possible implementation of the first embodiment, the data processing performed on raw APC data by the data processing unit 110 is carried out by applying a median filter followed by integrating multiple data points to smooth the data and subtract a baseline level to remove the offset. Other types of data processing on the raw biosensor data and the raw APC data by the data processing unit 110 may be envisioned by those skilled in the art, without departing from the spirit and scope of the invention.

The PCA unit 130 performs Principal Component Analysis, which is a statistical technique known in the mathematical arts used to reduce multidimensional data sets to lower dimensions for analysis. PCA involves the calculation of an Eigenvalue decomposition or a Singular value decomposition of a data set. The results of a PCA are usually discussed in terms of component scores and loadings. PCA is mostly used for making predictive models. In the first embodiment, PCA is used as a tool to reduce the multi-dimensional biosensor data to a one-dimension score vs. time. The score is of one of the principal components captured in the biosensor data, but it is typically of the first or second one. The relationship of score vs. time is then utilized to detect a correlated signal response from the biosensors.

For conventional biosensor analysis systems, a standard data set is typically used to generate a PCA model onto which unknown data is projected, in order to obtain the prediction. The PCA model of such conventional systems can be calibrated with an updated standard dataset if there is any change in operational conditions. In the first embodiment, however, no use is made of a standard dataset for calibration in its real-time model. Instead, a PCA is applied for every data point, and decision-making is performed based on the comparison between the latest change in score and the score variation in a background window. A reference model generated with the background window is updated for every data point and is considered as being calibrated in real-time. This enhances the robustness of the statistical analysis performed by the PCA model (as performed by the PCA unit 130) according to the first embodiment.

The system and method according to the first embodiment exploit the change in the value of the score to detect a non-specific response signal instead of the principal component vector for specific pattern recognition and prediction. A non-specific response signal may be caused by any analytes of interest, interferents, high level of noise, or changes in operational conditions. Only a positive result at the statistical analysis step (as performed by the PCA unit 130) will trigger the next step of numerical pattern recognition for bioalarm, as performed by the numerical analysis units 140, 150, 160 and 170.

In the first embodiment, the PCA is only performed on the biosensor data, and is not performed on the APC data, as seen by the direct path between the processed data store 120 and the Interferent Rejection II unit 160 in FIG. 1. Biosensor data stored in the processed data store 120 is subject to statistical analysis as performed by the PCA unit 130, and then that statistically analyzed data is provided to the Interferent Rejection I unit 140.

The numerical analysis performed by the numerical analysis units 140, 150, 160 is essentially a pattern recognition process. It is executed only if a positive result is obtained (e.g., a response signal is generated) by the PCA unit 130. For the numerical analysis, each pattern is characterized with a set of vectors of which each is associated with a particular sensor/detector type. Each vector is assigned a logic value of +1, 0, or −1. The assignment of the logic values according to one possible numerical analysis implementation is described below.

For biosensor data,
If the biosensor data meet the following condition, +1 is assigned to the relevant vector:

$1^{st}$ derivative of $(P_{t-2}, P_{t-1}, P_t)$ − $1^{st}$ derivative of $(P_{t-5}, P_{t-4}, P_{t-3}) \geq$ positive threshold where $P_t$ is the current data point and $P_{t-1}$ is the point before, etc., and $(P_{t-2}, P_{t-1}, P_t)$ defines the detection window, and $(P_{t-5}, P_{t-4}, P_{t-3})$ is considered the background window.

If the biosensor data meet the following condition, −1 is assigned to the relevant vector:

$1^{st}$ derivative of $(P_{t-2}, P_{t-1}, P_t)$ − $1^{st}$ derivative of $(P_{t-5}, P_{t-4}, P_{t-3}) \geq$ negative threshold Otherwise, 0 is assigned to the vector.
For APC data,
If a net increase in APC (current APC level−baseline level) is larger than a positive threshold, +1 is assigned to the vector.
If a net decrease in APC (current APC level−baseline level) is less than a negative threshold, −1 is assigned to the vector.
Otherwise 0 is assigned to the vector.

The logical values are combined into vectors to form a pattern. The number of vectors used to express a pattern is equal to the number of sensor/detector types in the system. By way of example, there are four (4) biosensor types (S1, S2, S3, S4) and one (1) APC detector (APC1) in a sensor array. Formation of a pattern is as described below:

| Vectors | Combined pattern |
|---|---|
| S1 (+1, 0, −1) | |
| S2 (+1, 0, −1) | [S1 (+1, 0, −1), S2 (+1, 0, −1), |
| S3 (+1, 0, −1) | S3 (+1, 0, −1), S4 (+1, 0, 1), APC1 (+1, 0, −1)] |
| S4 (+1, 0, −1) | |

Only a subset of the combined patterns is related to analytes of interest. In one possible implementation of the first embodiment, the following three conditions are used to determine whether or not a pattern is related to an analyte:

The combined pattern does not contain generic features of interferent patterns. (interferent rejection I unit 140)

The combined pattern captures generic features of the known analyte patterns (biological match unit 150).

The APC vector is +1. (interferent rejection II unit 160)

The interferent and analyte generic pattern features described above are extracted from data that can be collected from in-house or from field system tests. In the first embodiment, a model is created for checking each of the three conditions listed above. The numerical models can be run sequentially or in parallel, but all of the conditions should be met to trigger a bioalarm. In the first embodiment, sequential checking is performed by the three numerical analysis units 140, 150, 160 to determine if the above three conditions have been met, to reduce redundant computing. Alternatively, the processing performed by the numerical analysis units 140, 150, 160 can be performed in parallel, depending upon the type of processor or processors used to perform the numerical analyses of the biosensor and APC data.

If the three conditions described above have all been met, a bioalarm will be issued, and this issuance will initiate the classification of the data by the classification sensor data unit 170, whereby more detailed pattern recognition is carried out. Also, other data signatures, such as a difference in response time between certain sensor types, can be analyzed by the classification sensor data unit 170 to identify the detected bioagent as belonging to one of different classes of bioagents, such as one of the following classes: bacterial spores, bacteria, viruses, and toxins.

Figure 2:
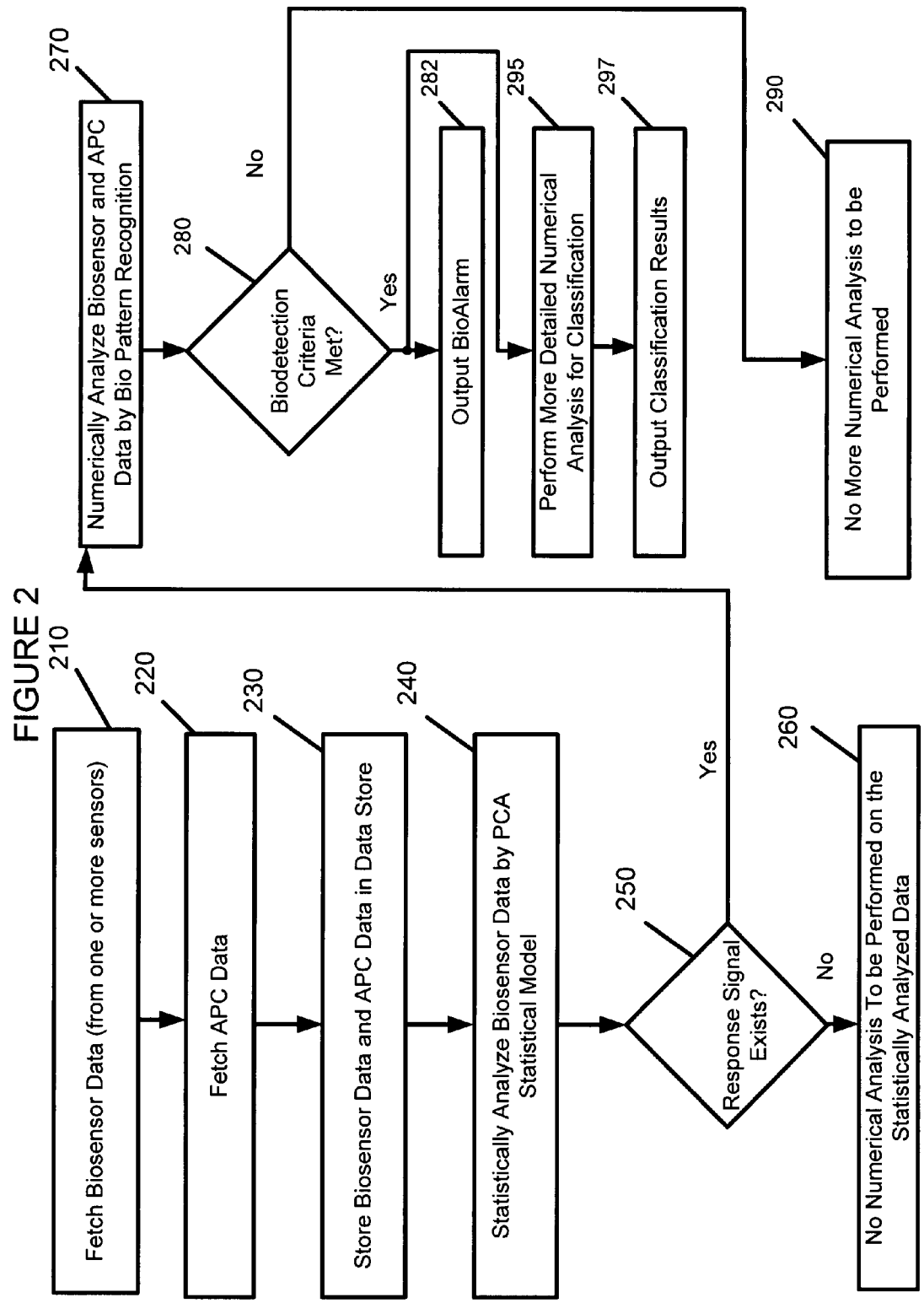
FIG. 2 is a flow diagram diagramming a method of performing biosensor array detection and classification, according to the first embodiment.

FIG. 2 shows a method of performing biosensor array detection and classification, according to the first embodiment. In a first step 210, biosensor data is collected, whereby such biosensor data may be obtained from one or more array of sensors. In a second step 220, which is typically performed at the same time as the first step 210, APC data is collected. In a third step 230, the biosensor data and the APC data are stored in a data store. In a fourth step 240, the biosensor data is statistically analyzed by a Principle Component Analysis (PCA) statistical model, to determine if there is a response signal. In a fifth step 260, a determination is made as to whether or not a response signal exists in the biosensor data. If no response signal exists, then in a sixth step 260, no further steps are performed (no numerical analysis is performed. If a response signal is determined to exist, then in a seventh step 270, the biosensor data and the APC data is subject to one or more numerical models, in order to categorize that data as biological or non-biological detection. Then, in an eighth step 280, a determination is made as to whether or not the categorization results meet certain criteria. If Yes, a bioalarm is output in step 282, a more detailed classification of the biosensor data is made in step 295 and the classification result is output in step 297 (note that steps 282 and 295 can be initiated at the same time). If No, in step 280, no further numerical analysis is performed on the biosensor data, as shown in step 290.

The embodiments described above have been set forth herein for the purpose of illustration. This description, however, should not be deemed to be a limitation on the scope of the invention. Various modifications, adaptations, and alternatives may occur to one skilled in the art without departing from the claimed inventive concept. For example, in a second embodiment, only sensor data provided by an array of sensors or biosensors would be analyzed, and APC data would not be input and analyzed, whereby the numerical processing unit would include only the units 140, 150 and 170 in that instance. The spirit and scope of the invention are indicated by the following claims.

What is claimed is:

1. A method for detecting and classifying sensor data, comprising:

processing data collected from an array of sensors by using a data processing unit;

performing a statistical analysis of the data collected from the array of sensors, to obtain statistically analyzed sensor data by using a statistical analysis unit;

determining, based on the statistically analyzed sensor data, whether or not there a response signal has been generated from the array of sensors by using said statistical analysis unit; and performing, if a response signal is determined to have been generated, a numerical pattern recognition on the data collected from the array of sensors by using a numerical pattern recognition unit, in order to categorize the data, wherein the step of performing a numerical pattern recognition comprises:
  performing an interferent rejection pattern analysis on the sensor data;
  performing a biological match pattern analysis on the sensor data;
  performing an interferent rejection pattern analysis on airborne particle data; and
  performing a classification pattern analysis on the sensor data by using said numerical pattern recognition unit.

2. The method according to claim 1, wherein the step of performing a statistical analysis is performed by using a principle component analysis statistical model.

3. The method according to claim 1, wherein, based on results obtained from performing a numerical pattern recognition, outputting an alarm if the data collected from the array of sensors is determined to be provided by one of a predetermined set of bioagents.

4. A method for detecting and classifying sensor data, comprising:
  processing data collected from an array of sensors by using a data processing unit;
  performing a statistical analysis of the data collected from the array of sensors, to obtain statistically analyzed sensor data by using a statistical analysis unit;
  determining, based on the statistically analyzed sensor data, whether or not there a response signal has been generated from the array of sensors by using said statistical analysis unit;
  performing, if a response signal is determined to have been generated, a numerical pattern recognition on the data collected from the array of sensors, in order to categorize the data by using a numerical pattern recognition unit; and
  processing airborne particle data from one or more other sensors,
  wherein the step of performing a numerical pattern comprises:
    performing a first interferent rejection pattern analysis on the sensor data;
    performing a biological match pattern analysis on the sensor data;
    performing a second interferent rejection pattern analysis on the airborne particle data; and
    if the results of the three performing steps meet predetermined criteria, performing a classification pattern analysis on the sensor data by using said numerical pattern recognition unit.

5. The method according to claim 4,
wherein the step of performing a statistical analysis is performed on the data collected from the array of sensors and not on the airborne particle data.

6. The method according to claim 4, wherein the step of performing a first interferent rejection pattern analysis is performed on a combination of the statistically sensor data and on raw sensor data that has not been statistically analyzed.

7. A system for detecting and classifying sensor data, comprising:
  a data processing unit configured to receive and perform data processing on data output from an array of sensors;
  a statistical analysis unit configured to perform statistical analysis on the data collected from the array of sensors and data processed by the data processing unit, to obtain statistically analyzed sensor data, wherein the statistical analysis unit determines, based on the statistically analyzed sensor data, whether or not there a response signal has been generated from the array of sensors; and
  a numerical pattern recognition unit configured to perform a numerical pattern recognition on the data collected from the array of sensors, in order to categorize the data,
  wherein the numerical pattern recognition unit comprises:
    an interferent rejection pattern analysis unit configured to perform an interferent rejection pattern analysis on the sensor data;
    a biological match pattern analysis unit configured to perform a biological match pattern analysis on the sensor data; and
    a classification unit configured to perform a classification pattern analysis on the sensor data.

8. The system according to claim 7, wherein the numerical pattern recognition unit only performs the numerical pattern recognition when the response signal is determined to have been generated.

9. The system according to claim 7, further comprising:
  a second data processing unit configured to receive and perform data processing on airborne particle data output from one or more other sensors,
  wherein the statistical analysis unit performs statistical analysis on the data collected from the array of sensors and not on the airborne particle data.

10. The system according to claim 7, wherein the statistical analysis unit performs statistical analysis using a principle component analysis statistical model.

11. A system for detecting and classifying sensor data, comprising:
  a first data processing unit configured to receive and perform data processing on data output from an array of sensors;
  a statistical analysis unit configured to perform statistical analysis on the data collected from the array of sensors and data processed by the first data processing unit, to obtain statistically analyzed sensor data, wherein the statistical analysis unit determines, based on the statistically analyzed sensor data, whether or not there a response signal has been generated from the array of sensors;
  a numerical pattern recognition unit configured to perform a numerical pattern recognition on the data collected from the array of sensors, in order to categorize the data; and
  a second data processing unit configured to receive and perform data processing on airborne particle data output from one or more other sensors,
  wherein the statistical analysis unit performs statistical analysis on the data collected from the array of sensors and not on the airborne particle data,
  wherein the step of performing a numerical pattern comprises:
    a first interferent rejection pattern analysis unit configured to perform a first interferent rejection pattern analysis on the sensor data;
    a biological match pattern analysis unit configured to perform a biological match pattern analysis on the sensor data;
    a second interferent rejection pattern analysis unit configured to perform a second interferent rejection pattern analysis on the airborne particle data; and
    a classification unit configured to perform a classification pattern analysis on the sensor data, when the results of the first and second interferent rejection pattern analyses and the biological match pattern analysis meet predetermined criteria.

12. The system according to claim 11, wherein the first interferent rejection pattern analysis unit performs the first interferent rejection pattern analysis on a combination of the statistically sensor data and on raw sensor data that has not been statistically analyzed.

13. The system according to claim 11, further comprising:
an alarm unit communicatively connected to the numerical pattern recognition unit,
wherein, based on data provided by the numerical pattern recognition unit, the alarm unit outputs an alarm if the data collected from the array of sensors is determined to be provided by one of a predetermined set of bioagents.

14. A computer readable medium embodying computer program product for detecting and classifying sensor data, the computer program product, when executed by a computer, causing the computer to perform the steps of:
fetching data from an array of sensors;
performing a statistical analysis of the data collected from the array of sensors, to obtain statistically analyzed sensor data;
determining, based on the statistically analyzed sensor data, whether or not there a response signal has been generated from the array of sensors; and
performing, if a response signal is determined to have been generated, a numerical pattern recognition on the data collected from the array of sensors, in order to categorize the data,
wherein the step of performing a numerical pattern recognition comprises:
performing an interferent rejection pattern analysis on the sensor data;
performing a biological match pattern analysis on the sensor data; and
performing a classification pattern analysis on the sensor data.

15. The computer readable medium according to claim 14, further comprising:
fetching airborne particle data from one or more other sensors,
wherein the step of performing a statistical analysis is performed on the data collected from the array of sensors and not on the airborne particle data.

16. The computer readable medium according to claim 14, wherein the step of performing a statistical analysis is performed by using a principle component analysis statistical model.

17. The computer readable medium according to claim 14, wherein the statistical analysis performed in the performing step is a Principle Component Analysis.

18. A computer readable medium embodying computer program product for detecting and classifying sensor data, the computer program product, when executed by a computer, causing the computer to perform the steps of:
fetching data from an array of sensors;
performing a statistical analysis of the data collected from the array of sensors, to obtain statistically analyzed sensor data;
determining, based on the statistically analyzed sensor data, whether or not there a response signal has been generated from the array of sensors;
performing, if a response signal is determined to have been generated, a numerical pattern recognition on the data collected from the array of sensors, in order to categorize the data; and
fetching airborne particle data from one or more other sensors,
wherein the step of performing a statistical analysis is performed on the data collected from the array of sensors and not on the airborne particle data,
wherein the step of performing a numerical pattern comprises:
performing a first interferent rejection pattern analysis on the sensor data;
performing a biological match pattern analysis on the sensor data;
performing a second interferent rejection pattern analysis on the airborne particle data; and
if the results of the three performing steps meet predetermined criteria, performing a classification pattern analysis on the sensor data.

19. The computer readable medium according to claim 18, wherein the step of performing a first interferent rejection pattern analysis is performed on a combination of the statistically sensor data and on raw sensor data that has not been statistically analyzed.

* * * * *